United States Patent [19]

Kalayjian

[11] Patent Number: 4,724,922

[45] Date of Patent: Feb. 16, 1988

[54] ACOUSTIC EARPIECE

[76] Inventor: Robert W. Kalayjian, Rte. 8, Box 65A, Turkey Farm Rd., Chapel Hill, N.C. 27514

[21] Appl. No.: 890,087

[22] Filed: Jul. 24, 1986

[51] Int. Cl.[4] .................... A61B 7/02

[52] U.S. Cl. .................... 181/135; 181/130

[58] Field of Search .................... 181/135, 130; 128/152; 381/68.6

[56] References Cited

U.S. PATENT DOCUMENTS

| | | | |
|---|---|---|---|
| 3,080,011 | 3/1963 | Henderson . | |
| 3,169,600 | 2/1965 | Thomas | 181/135 |
| 3,303,902 | 2/1967 | Knott | 181/135 |
| 3,539,032 | 11/1970 | Scanlon | 181/135 |
| 3,811,437 | 5/1974 | Gardner, Jr. | 128/152 |
| 3,881,570 | 5/1975 | Lewis . | |
| 3,882,848 | 5/1975 | Klar et al. . | |
| 4,006,796 | 2/1977 | Coehorst | 181/135 X |
| 4,177,871 | 12/1979 | Clanton | 181/131 |
| 4,193,396 | 3/1980 | Wacker | 128/152 |
| 4,253,452 | 3/1981 | Powers et al. | 128/152 |
| 4,347,911 | 9/1982 | Bertagna et al. | 181/130 |
| 4,420,657 | 12/1983 | Larkin . | |
| 4,554,993 | 11/1985 | Houng | 181/130 |

*Primary Examiner*—Benjamin R. Fuller
*Attorney, Agent, or Firm*—Richard E. Jenkins

[57] ABSTRACT

An improved acoustic earpiece of the type used to transmit sound mechanically from a sound source to the ear drum of a listener is disclosed herein. The acoustic earpiece includes a tube and a resilient element surrounding one end thereof comprising an open cell resilient foam with a slow compression recovery rate and a fully compressed diameter of less than the diameter of the human ear canal.

6 Claims, 6 Drawing Figures

ACOUSTIC EARPIECE

DESCRIPTION

1. Technical Field

The present invention relates to an improved acoustic earpiece, and more particularly to an earpiece for use in transmitting sound mechanically from a sound source to an ear of a listener.

2. Background Art

The background art discloses a number of attempts to provide sound headsets for efficiently and comfortably transmitting or conveying sound waves directly from a sound source through a hollow tube to the ear of the listener. Although certainly not all inclusive, the sound headsets include those used with stethoscopes and headsets utilized in public-transport vehicles such as jet aircraft and the like. However, all of the acoustic headsets known to the applicant suffer from a variety of shortcomings which impair the quality of sound transmitted to the user or which result in user discomfort due to the method of securement of the earpiece to the ear.

For example, U.S. Pat. No. 3,080,011 discloses an ear canal insert comprising a plurality of soft rubber or plastic annular flanges fitted over a mounting tube and insertable into the ear canal. Although the soft flanges tend to fold inwardly, the wedge-type fit creates contact with the ear canal only in a series of narrow spaced-apart rings and thereby necessitates application of relatively high pressure over a small area of the ear canal to accomplish an air-tight fit. In addition to being uncomfortable, this type of ear canal insert is not very effective in reducing ambient noise from gaining entrance to the ear canal. Another general type of prior art headset is disclosed in U.S. Pat. No. 4,347,911, U.S. Pat. No. 3,169,600 and U.S. Pat. No. 3,539,032 and provides a foam cushion concentrically positioned around the terminal end of a sound tube in order to attempt to form a seal with the Concha or outer ear around the opening to the ear canal. These types of headsets also tend to be somewhat uncomfortable to the user and do not form an effective seal in order to minimize ambient noise.

DISCLOSURE OF THE INVENTION

In accordance with the present invention, applicant provides an acoustic earpiece of novel construction which is more comfortable and more efficient in reducing ambient noise from gaining entrance to the ear canal than has heretofore been possible. The acoustic earpiece includes a small diameter, sound-transmitting, flexible tube connected at one end to a sound source and having an open cell resilient foam element secured to the other end thereof which has a slow compression recovery rate and a fully compressed diameter of less than the diameter of the human ear canal. Preferably the sound tube is about 0.09 inches in outside diameter (0.06 inches internal diameter), and the resilient foam element is constructed of EAR or HYPOL foam material with the terminal end of the sound tube being flared radially outwardly. The acoustic earpiece of the invention thereby is adapted so that it may be compressed into an elongate shape with a diameter less than the ear canal diameter. It may then be inserted into the ear canal and allowed to expand into sealing engagement therewith. The expanded foam applies a gentle, low pressure contact over a wide circumferential band or surface area within the ear canal which serves to both effectively seal the ear canal from ambient sound and render the earpiece comfortable to a user thereof.

It is therefore an object of the present invention to provide an acoustic earpiece which will provide better mechanical sound transmission than has heretofore been possible.

Another object of the present invention is to provide an acoustic earpiece which forms an improved seal in the ear canal in order to better prevent entry of ambient sound or noise into the ear canal.

Still another object of the present invention is to provide an acoustic earpiece which while providing an improved seal with the ear canal is still comfortable to a user of the earpiece.

Some of the objects of the invention having been stated, other objects will become evident as the description proceeds, when taken in connection with the accompanying drawings.

BEST MODE FOR CARRYING OUT THE INVENTION

Figure 1:
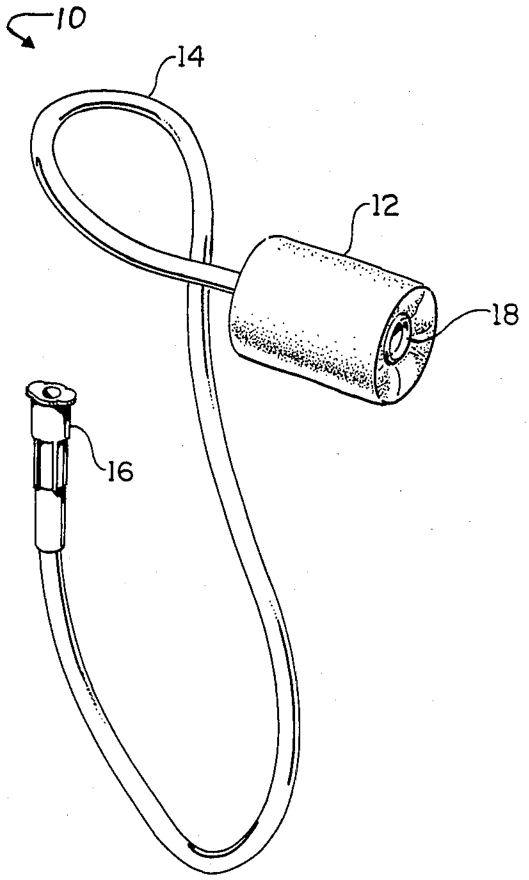
FIG. 1 is a view in perspective showing an acoustic earpiece embodying the invention.
Figure 2:
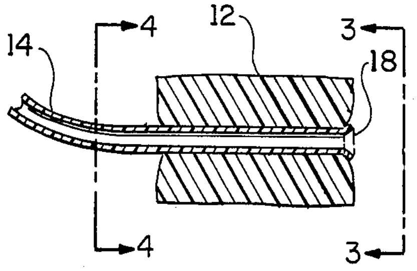
FIG. 2 is a view in axial section through the acoustic earpiece of FIG. 1.
Figure 3:
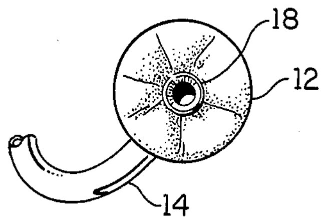
FIG. 3 is a front elevation view of the acoustic earpiece of FIG. 1.
Figure 4:
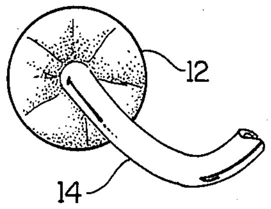
FIG. 4 is a rear elevation view of the acoustic earpiece of FIG. 1.

Referring now more specifically to the drawings, a preferred embodiment of an acoustic earpiece according to the present invention is shown in FIGS. 1–4 and generally designated 10. Acoustic earpiece 10 includes foam element 12, flexible tube 14 with flared end 18, and a jack 16 (optional) which may be plugged into a suitable sound source such as a sound collector, transducer or sound receiver (not shown). For example, jack 16 may be connected to a stethoscope bell to aid a physician in listening to a patient's heart or may be attached to a remote speaker of the type utilized on an airplane in order to provide the passengers with audio entertainment without disturbing other passengers who may not wish to be disturbed.

In order to best understand the acoustic earpiece of the present invention, certain basics of sound transmittal and human ear biology should be appreciated. First of all, in order to transmit sound in a small diameter tube, the sound must be generated by longitudinal compression waves which are created when a sound source sealingly engages one end of the tube. In a similar fashion, the other end of the tube should be in sealing engagement with the ear canal in order to assure that the compression waves are transferred directly to the tympanic membrane or ear drum. Any leak in this type of system significantly reduces the efficiency of the sound transmission from the sound source to the ear drum.

With a device which connects the human ear to a source of sound with a flexible plastic-type tube, it is possible to transmit the sound over a considerable distance with minimal loss. Although the output of the sound source may be small (for example, a human heart beat or the electronic speaker in a hearing aid), the transmission can be highly efficient even through tubing which is in a non-linear configuration. However, it has been found that the tubing must be reasonably rigid and that the diameter should be smaller than the ear canal diameter but large enough for the sound energy carried into the ear canal to set the ear drum in motion. Most tubing with an internal diameter between 0.05 inches and 0.20 inches is effective in transmitting sound. However, it is essential to faithful mechanical sound transmission that the sound source, the tubing and the ear canal be in a closed or sealed relationship. Any leaks or openings in the sound transmission system from the source to the ear canal will be detrimental to the efficiency of the compression wave transmittal.

The ear canal or auditory meatus of a human is approximately 1.25 inches long and has a variable diameter at its opening of between about 0.18 and 0.50 inches which narrows as it approaches the ear drum or tympanic membrane. The outer third of the length of the ear canal has an internal wall covered with coarse hairs growing in an outward direction and glands which secrete cerumen or wax. The purpose of the hair and wax secretions is, of course, to trap foreign materials or insects at the entry portion of the ear canal and to thereby prevent contamination of the ear drum and inner canal.

With an understanding of the above, it can now be fully appreciated that the purpose of acoustic earpiece 10 is to create an air-tight seal between the ear canal and flexible tube 14 in order to optimize transmission of sound from a sound source (not shown) to which jack 16 is sealingly connected. Acoustic earpiece 10 accomplishes the aformentioned air-tight seal without the discomfort, injury and disease known to accompany earpieces of previous designs as will be more fully explained hereinafter.

Figure 6:
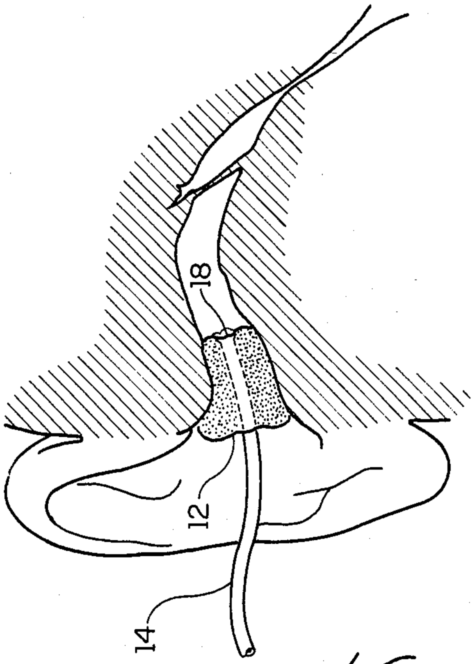
FIG. 6 is a diagrammatic view illustrating the acoustic earpiece of FIG. 5 after it has expanded to engage the circumference of a portion of the ear canal of a user thereof.
Figure 5:
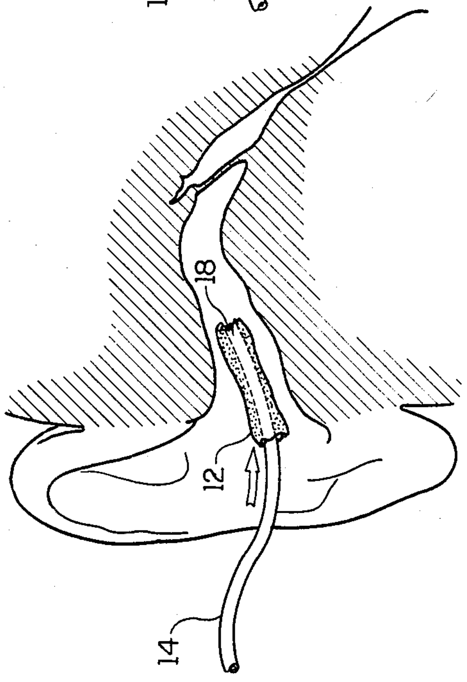
FIG. 5 is a diagrammatic view illustrating an acoustic earpiece embodying the invention which has been compressed and is being inserted into the ear canal of a user.

With reference now to FIGS. 5 and 6, acoustic earpiece 10 may be more fully understood. FIG. 5 illustrates acoustic earpiece 10 in its fully compressed state being inserted inwardly into the ear canal of a user. FIG. 6 illustrates the acoustic earpiece properly positioned and seated in the ear canal of a user. As can be seen, it is in sealing engagement with a relatively large surface area of the ear canal or, stated in another way, the width of the band of contact between foam element 12 and the inner surface of the ear canal is a relatively wide ring. This tends to distribute the radial pressure exerted by foam element 12 in its sealing engagement with the ear canal over a large surface area in order to minimize the pressure applied at a given point to accomplish an air-tight fit. In contradistinction to earpieces utilized in the past, acoustic earpiece 10 increases the contact area between the ear canal and foam element 12 as opposed to increasing the pressure between the ear canal and an earpiece. The result is an acoustic earpiece which forms an effective seal with the ear canal without the discomfort of previous earpieces. Furthermore, the relatively low pressure applied to the ear canal by earpiece 10 is not sufficient to occlude sebaceous or wax secreting glands or to turn inward the hairs in the ear canal. This is advantageous since pressure against the skin in the ear canal can occlude the opening of the wax secreting and sebaceous glands and damage the glands by increasing pressure inside thereof. Likewise, the trapping of bacteria in an occluded gland can result in an infection of the gland called a furuncle or "boil", and persistent pressure against hair folicles traps bacteria in the folicle and may result in an infection called "folliculitis". It is important, therefore, that the wax, hairs, bacteria, and desquamated or shedded skin cells in the ear canal be allowed to migrate outside thereof.

Foam element 12 is most suitably formed from a moderately damped foam plastic such as EAR material manufactured by Cabot Corporation or HYPOL material manufactured by W. R. Grace Company, and has an uncompressed diameter of about 0.55 inches. Foam element 12 may be compressed substantially and will re-expand into sealing engagement with the ear canal of a user within about 1–30 seconds. Moreover, foam element 12 is inexpensive and may be easily replaced as necessary.

Flexible tube 14 is most preferably a clear, flexible vinyl tubing (such as manufactured by Almac Corporation) with an internal diameter of about 0.053 inches and a wall thickness of about 0.016 inches which has been found to be sufficiently large for good sound conduction but still small enough to allow fully compressed foam element 12 to be of a necessarily small diameter of not more than about 0.18 to 0.50 inch in order to be easily insertable into a human ear canal. This is a significant aspect of the invention since proper use of acoustic earpiece 10 requires that foam element 12 be initially compressed and, while still compressed, inserted relatively deeply into the ear canal where foam element 12 will expand and form a sealing engagement. If either flexible tube 14 or foam element 12 were so constructed that the fully compressed foam element 12 was larger than about 0.18 to 0.50 inch in diameter, the foam earpiece would not be properly insertable into the ear canal to form the efficient and comfortable seal provided by acoustic earpiece 10. Flexible tube 14 also most suitably defines flare 18 at the ear end thereof to better maintain element 12 on flexible tube 14 when acoustic earpiece 10 is removed from an ear. As a matter of design choice, flexible tube 14 may be constructed with the end segment thereof which is positioned within foam element 12 being formed of a rigid plastic or other suitably rigid material to best support foam element 12.

Acoustic earpiece 10 does not tend to push wax and foreign material inwardly into the ear canal as do other earpieces when they are forced into the ear in an attempt to form a seal. Moreover, the porous surface of foam element 12 actually tends to absorb ear wax and debris while in place. Finally, applicant would like to point out that acoustic earpiece 10 provides a seal in the human ear canal which has a higher coefficient of friction than other earpieces due to its substantially larger area of contact with the inner ear surface and the porosity of foam element 12. This aids in maintaining acoustic earpiece 10 in place during use thereof.

In operation, foam element 12 of acoustic earpiece 10 is compressed and carefully inserted into a selected ear canal by a user. It is allowed to expand and form a sealing engagement with the ear canal prior to use. Jack 16 is sealingly connected to a sound source and acoustic earpiece 10 is then ready for use. Good hygiene would require that foam element 12 be replaced after 5–20 hours of use in view of the ear wax collected thereon. When a user desires to remove foam element 12 of acoustic earpiece 10 from his ear, flexible tube 14 is engaged immediately behind foam element 12 and a gentle tugging force exerted outwardly thereon in order to comfortably remove foam element 12 from the ear canal.

Although acoustic earpiece 10 has been described as a singular unit for use in one ear of a user, it should be apparent that the invention fully contemplates other embodiments of the inventive earpiece which simultaneously utilize two of the earpieces for comfortably and efficiently conveying sound from a sound source to both ears of a user.

Having shown and described a preferred embodiment of the present invention, by way of example, it should be realized that structural changes could be made and other examples given without departing from either the spirit or scope of this invention.

What is claimed is:

1. An acoustic earpiece adapted to be sealingly inserted into an ear canal of an ear of a user for mechanically transmitting sound from a source through a sound transmitting tube to the ear of the user, comprising:

a sound transmitting tube having a diameter substantially smaller than the diameter of the external ear canal and an outwardly flared end; and a resilient member consisting of urethane foam surrounding said flared end of said tube, said foam member defining a cylindrical element having a slow compression recovery rate and a compressed diameter of no greater than about 0.18 to 0.50 inches, whereby said compressed earpiece may be inserted into the ear canal of the ear of the user and will thereupon expand to form an elongate sound seal therein with a substantial surface area of the ear canal.

2. A acoustic earpiece according to claim 1 wherein said tube comprises a flexible plastic tube having an internal diameter of about 0.06 inches and an external diameter of about 0.09 inches.

3. An acoustic earpiece according to claim 1 wherein the end portion of said tube surrounded by said resilient member is rigid and the remaining length of said tube is flexible.

4. An acoustic earpiece according to claim 1 wherein said foam element requires about 1 to 30 seconds to recover from a compressed condition and form a sound seal in the ear canal of the user.

5. An acoustic earpiece according to claim 4 wherein said foam element has a fully expanded diameter of about 0.55 inches when not is use.

6. An acoustic earpiece according to claim 1 wherein said earpiece includes a female adaptor on the other end of said tube to accommodate use thereof as an anesthesia stethoscope earpiece.

* * * * *